United States Patent
Boyle et al.

(10) Patent No.: US 8,319,177 B2
(45) Date of Patent: *Nov. 27, 2012

(54) ION MOBILITY SPECTROMETER

(75) Inventors: Paul Boyle, London (GB); Andrew H. Koehl, Cambridge (GB); David Ruiz-Alonso, Cambridge (GB)

(73) Assignee: Owlstone Ltd., Cambridge (GB)

(*) Notice: Subject to any disclaimer, the term of this patent is extended or adjusted under 35 U.S.C. 154(b) by 163 days.

This patent is subject to a terminal disclaimer.

(21) Appl. No.: 12/774,869

(22) Filed: May 6, 2010

(65) Prior Publication Data

US 2011/0006196 A1    Jan. 13, 2011

Related U.S. Application Data

(63) Continuation of application No. 11/659,262, filed as application No. PCT/GB2005/050124 on Aug. 2, 2005, now Pat. No. 7,714,278.

(30) Foreign Application Priority Data

Aug. 2, 2004  (GB) .................................. 0417184.9
Jan. 17, 2005 (GB) .................................. 0500812.3

(51) Int. Cl.
    *H01J 49/28* (2006.01)

(52) U.S. Cl. ......... 250/287; 250/281; 250/282; 250/290

(58) Field of Classification Search .................. 250/281, 250/282, 287, 290, 294
    See application file for complete search history.

(56) References Cited

U.S. PATENT DOCUMENTS

| | | | |
|---|---|---|---|
| 5,789,745 | A | 8/1998 | Martin et al. |
| 6,051,832 | A | 4/2000 | Bradshaw |
| 6,107,624 | A | 8/2000 | Doring et al. |
| 7,714,278 | B2 * | 5/2010 | Boyle et al. .................. 250/287 |
| 2002/0070338 | A1 | 6/2002 | Loboda |
| 2002/0117617 | A1 | 8/2002 | Sinha et al. |
| 2003/0089849 | A1 | 5/2003 | Guevremont et al. |

(Continued)

FOREIGN PATENT DOCUMENTS

EP     0692712 A1     1/1996

(Continued)

OTHER PUBLICATIONS

Miller et al., "A novel micromachined high-field asymmetric waveform ion mobility spectrometer" Sensors and Actuators B, Elsevier Sequoia S.A., Lausanne, CH, 67(3):300-306 (2000).

(Continued)

*Primary Examiner* — Michael Maskell
*Assistant Examiner* — Hanway Chang
(74) *Attorney, Agent, or Firm* — Edwards Wildman Palmer LLP; Barry Kramer; Christopher J. Capelli

(57) ABSTRACT

An ion mobility spectrometer is described having an ion filter in the form of at least one ion channel having a plurality of electrodes. A time-varying electric potential applied to the conductive layers allows the filler to selectively admit ion species. The electric potential has a drive and a transverse component, and in preferred embodiments each of the electrodes is involved in generating a component of both the drive and transverse fields. The device may be used without a drift gas flow. Microfabrication techniques are described for producing microscale spectrometers, as are various uses of the spectrometer.

20 Claims, 12 Drawing Sheets

U.S. PATENT DOCUMENTS

2003/0201398 A1    10/2003    Perkins
2004/0222371 A1    11/2004    Hartley

FOREIGN PATENT DOCUMENTS

| | | |
|---|---|---|
| JP | 08087976 A | 4/1996 |
| JP | 2001343360 A | 12/2001 |
| JP | 2003514349 A | 4/2003 |
| JP | 2003527734 A | 9/2003 |
| JP | 2007524405 A | 8/2007 |
| WO | WO-0164320 A1 | 9/2001 |
| WO | WO-02071053 A2 | 9/2002 |

OTHER PUBLICATIONS

Krylov, E.V., "Comparison of the planar and coaxial field asymmetrical waveform ion mobility spectrometer" International Journal of Mass Spectrometry 225:39-51 (2003.

International Search Report for PCT/GB2005/050124 mailed on Dec. 10, 2006 (4 pages).

International Preliminary Report on Patentability and the Written Opinion of the International Search Authority (ISA) for PCT/GB2005/050124) issued on Feb. 6, 2007 (11 pages).

* cited by examiner

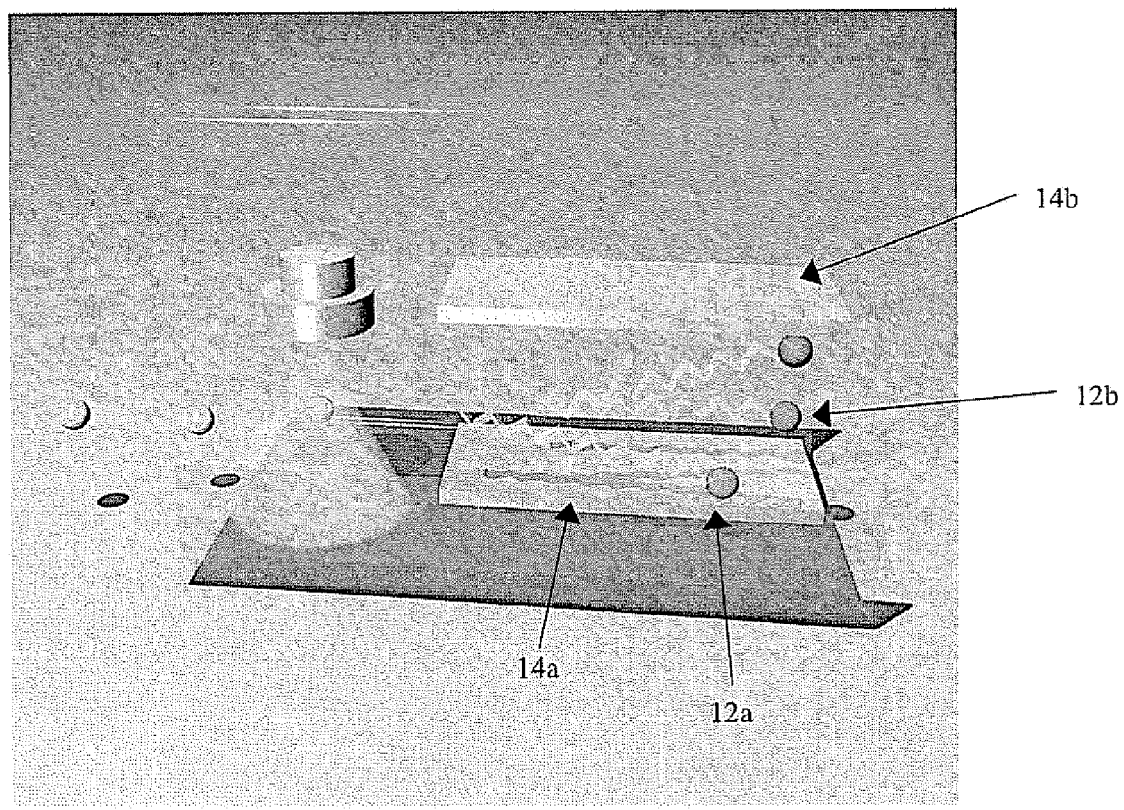
Figure 1, prior art.

ION MOBILITY SPECTROMETER

CROSS REFERENCE TO RELATED APPLICATIONS

This patent application is a continuation of and claims the benefit of priority from U.S. patent application Ser. No. 11/659,262, filed Aug. 2, 2005 as International Application No. PCT/GB05/50124, and issued as U.S. Pat. No. 7,714,278, which in turn claims the benefit of priority to British Patent Application No. GB 0417184.9, filed Aug. 2, 2004, and British Patent Application No. GB 0500812.3, filed Jan. 17, 2005. The disclosure of each of the aforementioned patents and patent applications is incorporated by reference herein in its entirety.

FIELD OF THE DISCLOSURE

The present disclosure relates to an ion mobility spectrometer, and more particularly to a field asymmetric ion mobility (FAIM) spectrometer. Certain aspects of the disclosed embodiments relate to a micro machined FAIM spectrometer. Aspects of the disclosed embodiments also relate to methods of performing ion mobility spectrometry, and to components for use in such a spectrometer.

BACKGROUND OF THE DISCLOSURE

Ion mobility spectrometry is a versatile technique used to detect the presence of molecular species in a gas sample. The technique has particular application in detection of explosives, drugs, and chemical agents in a sample, although it is not limited to these applications. Portable detectors are commonly used for security screening, and in the defense industry. However, conventional portable devices are still nonetheless relatively large.

Ion mobility spectrometry relies on the differential movement of different ion species through an electric field to a detector. By appropriate selection of the parameters of the electric field, ions having differing properties will reach the detector at differing times, if at all. Time of flight (TOF) ion mobility spectrometry measures the time taken by ions when subject to an electric field to travel along a drift tube to a detector against a drift gas flow. By varying the electric field, ions of different characteristics will reach the detector at different times, and the composition of a sample can be analyzed. This form of spectrometry relies on the length of the drift tube for its resolution; the longer the drift tube, the more powerful the detector. This restricts the possible miniaturization of such spectrometers, since there is a limit to the lower size of the drift tube which may effectively be used. Further, given that relatively high electric field strengths are necessary, the restriction on drift tube length also results in the need to use relatively high voltages in the device, which may be potentially hazardous to the operator and further restricts the possibility of miniaturization of the device.

A variation on TOF ion mobility spectrometry is described in U.S. Pat. No. 5,789,745, makes use of a moving electrical potential to move ions against a drift gas flow towards a detector. A plurality of spaced electrodes are alternately pulsed to generate a moving potential well, which carries selected ions along with it. This device is unsuited to miniaturization due to, among other reasons, the need for a pump to produce the drift gas flow.

Field asymmetric ion mobility spectrometry (FAIMS) is a derivative of time of flight ion mobility spectrometry (TOFIMS), which potentially offers a smaller form factor. Existing designs, however, use moving gas flows and high voltages, which are undesirable for microchip implementations. Scaling is further hindered by molecular diffusion, an effect that becomes significant in the micron regime. Background information relating to FAIMS can be found in L. A. Buryakov et al. Int. J. Mass. Spectrom. Ion Process. 128 (1993) 143; and E. V. Krylov et al. Int. J. Mass. Spectrom. Ion Process. 225 (2003) 39-51; hereby incorporated by reference.

Conventional FAIMS operates by drawing air at atmospheric pressure into a reaction region where the constituents of the sample are ionized. Chemical agents in vapor-phase compounds form ion clusters when they are exposed to their parent ions. The mobility of the ion clusters is mainly a function of shape and weight. The ions are blown between two metal electrodes, one with a low-voltage DC bias and the other with a periodic high-voltage pulse waveform, to a detector plate where they collide and a current is registered. Ions are quickly driven toward one electrode during the pulse phase and slowly driven toward the opposite electrode between pulses. Some ions impact an electrode before reaching the detector plate; other ions with the appropriate differential mobility reach the end, making this device a sort of differential mobility ion filter. A plot of the current generated versus DC bias provides a characteristic differential ion mobility spectrum. The intensity of the peaks in the spectrum, which corresponds to the amount of charge, indicates the relative concentration of the agent.

While this arrangement offers the possibility for greater miniaturization than conventional TOFIMS, the need to generate a gas flow requires the presence of a pump (diaphragm or similar) which using present technology limits the lower size of such a device. Representative examples of such devices are described in U.S. Pat. No. 6,495,823 and U.S. Pat. No. 6,512,224.

It would be of benefit to provide miniaturized ion mobility spectrometers for use in sensing techniques; not only would these be suitable for covert use or for large scale distribution, the smaller size will allow use of lower voltages in the device. Devices with no or fewer moving parts than conventional devices would also be of benefit, in that they would be more robust than conventional sensors, and so suitable for deployment in high-traffic areas or in harsh environments.

SUMMARY OF THE DISCLOSURE

The present inventors have developed a further modification of FAIMS, which does not require a drift gas flow for its operation. Instead, an electric field is used to cause ions to move toward the detector. This allows for a solid state construction which does not require a gas pump or similar, so allowing for greater miniaturization of the device than would otherwise be possible, as well as a more robust construction. The system as a whole can be reduced in size and cost, since no pump is necessary and the electronics may be reduced in size. Size reduction permits smaller gap sizes between electrodes and hence lower voltages, leading to smaller, more integrated electronics, more precise and controllable waveforms, and improved performance in terms of power usage and resolution. The spectrum of detected ions can provide information on multiple analytes simultaneously, since the ion filter is readily retunable simply by altering the electric field properties. Detection of additional analytes may be incorporated by altering the software controlling the filter and subsequent analysis, so making the system highly customizable.

Other advantages of the present disclosed embodiments include the reduction of false positives by adjustment of multiple parameters over time, which again may be achieved with software control. Many detectors may be networked together to combine outputs, to reduce the deleterious effects of local interferents and increase classification confidence, as well as to make the system as a whole more robust.

Finally, the exemplary disclosed embodiments are highly sensitive, allowing detection at trace levels, and rapid. With a reduced distance between ionizer and detector the time for which ions must exist to be detected is reduced, so allowing detection of short-lived ions. The system may be operated at low voltages, and at low power, allowing for longer operational use in a range of environments.

According to a first aspect of the present invention, there is provided an ion mobility spectrometer comprising an ionizer, an ion filter, and an ion detector; wherein the ion filter defines at least one ion channel along which ions may pass from the ionizer to the ion detector; and wherein the ion filter comprises a plurality of electrodes disposed proximate the ion channel; the spectrometer further comprising electrode control means for controlling the electrodes such that a first drive electric field is generated along the length of the ion channel, and a second transverse electric field is generated orthogonal to the first, and wherein each of said plurality of electrodes is involved in generating a component of both the drive and transverse electric fields. This arrangement allows for the drive electric field to be used to propel ions through the channel while the transverse electric field may be used to selectively affect the mobility of ions according to parameters such as their charge. Exemplary embodiments of a spectrometer in accordance with the present invention may therefore be used without a drift gas flow, and so requires fewer moving parts than conventional spectrometers.

In addition, a long drift tube is not necessary for exemplary embodiments made in accordance with the present invention to operate effectively. The drive and transverse electric fields are preferably applied simultaneously. Use of the same electrodes to generate components of both drive and transverse electric fields minimizes the number of electrodes needed, as well as reducing the size of the device. In certain embodiments of the invention, additional electrodes may however be present, and not all of the electrodes in the spectrometer need be involved in generating a component of both the drive and the transverse electric fields. The drive field is preferably a longitudinal electric field.

Preferably the drive electric field is a static electric field; that is, the field does not vary over time. However, a time-varying drive field can be employed, for example, to adjust the width of the resolution peaks and thus configure an instrument for optimum performance in a particular application. In some instruments the field may be swept and data collected over a range of field strengths. In this way drive field strength may be used as a further parameter for post-processing to achieve enhanced (more accurate) results. The field may be generated by application of a DC bias across the electrodes. It has been found that a continuous, static electric field is sufficient to drive ions along the ion channel while the transverse field separates the ions according to mobility, and hence parameters such as shape, mass and charge; this combination of fields removes the need for a drift gas flow.

The transverse electric field may vary over time, and may be generated by application of an AC voltage across the electrodes. The AC voltage is preferably asymmetric. Thus, in preferred embodiments of the invention, the transverse electric field comprises an AC component and a DC component. The DC component is preferably opposed to the AC component; that is, the AC component will tend to drive ions towards one side wall of the ion channel, while the DC component will tend to drive the ions towards the other side wall of the channel. A DC ramp or sweep voltage may also be added and parameters of the AC voltage such as amplitude, duty cycle and the like may also varied to obtain sweep and improve sensitivity and selectivity or other effects.

The electrode control means preferably allows any or all of the electric fields to be varied; this allows for the field to be tuned in order to permit detection of particular ions. Preferably the electrodes are disposed adjacent the entrance and exit to the ion channel. Alternatively the electrodes may be disposed within the channel itself.

At least two electrode pairs may be provided; one electrode is conveniently situated at each corner of the channel. That is, four electrodes form four electrode pairs: two transverse pairs which serve to generate a transverse field, and two longitudinal pairs which generate a drive field. Each electrode is a member of two pairs, one transverse pair and one drive pair. The electrode pairs are transversely separated by the channel itself, while the pairs may be vertically separated by a resistive (eg 1-100KΩcm resistive silicon) semiconducting or insulating material to provide structural stability. Preferably four electrodes are provided at each ion channel.

The ionizer may comprise any convenient means; for example, a source of ionizing radiation, a UV source, or the like.

The filter preferably comprises a plurality of ion channels, and conveniently more than 5, more than 10, more than 15, and more than 20 ion channels. The channels may conveniently be defined by a plurality of electrode fingers forming a comb-like arrangement. In preferred embodiments, the filter comprises two or more interdigitated electrode arrays, each array having a plurality of electrode fingers. The presence of multiple ion channels permits a relatively large ionization volume to be used adjacent the channels, thereby improving sensitivity of the spectrometer compared with conventional devices having a single ion channel and hence restricted to a relatively small ionization volume.

Preferably the ion channels are elongate; that is, they have a relatively short length (the direction along which ions will flow) and a relatively short width (in a minor transverse direction), with a relatively long depth (in a major transverse direction).

Optionally, the interdigitated fingers may be curved, more particularly serpentine, and in this way may then define curved or serpentine channels. This has the advantage of reducing diffusion losses which, with straight electrodes, are caused by ions diffusing into the walls of the channels. With curved or serpentine electrodes these diffusion losses are reduced (and the channel width in this sense is effectively increased) because of the formation of a partial potential well within a channel. Curved or serpentine channels also reduce the deleterious effects of space charge repulsion.

Thus in another aspect the invention provides an ion filter having channels defined by electrodes with this general formation. Also provided is an ion filter comprising two interdigitated electrodes forming a plurality of ion channels. Such an arrangement may be used as described, or with a drift gas flow; the smaller gap size provided by the interdigitated filter arrangement still provides advantages of reduced voltages and hence simpler control electronics even when a drift gas flow is used.

The filter preferably comprises a resistive or semiconductive substrate on which is provided a conductive surface to form an electrode. A conductive surface may be disposed on two faces of the substrate. The substrate may comprise silicon. The conductive surface may comprise metal, doped polysilicon or the like. In preferred embodiments, where the spectrometer is on a micro machined scale, the substrate and surface may conveniently be etched to form a desired shape and configuration, and to provide the ion channels, using conventional semiconductor processing techniques. This allows many channels to be formed in parallel, and on a small scale.

Preferably the length of the ion channel is less than the depth of the filter, and preferably significantly less; for example, at least 10 times less. In preferred embodiments, the filter has a generally wafer-like form, with the channel length being a fraction of the filter depth. In some preferred embodiments, the channel length is less than 1000 microns, less than 900 microns, and less than 800 microns, while the filter depth is more than 10,000 microns. Preferred channel length is from 1000 to 100 microns, more preferably from 800 to 300 microns, and most preferably from 500 to 300 microns.

Preferably also the width of the ion channel (that is, the gap spacing across the channel over which the transverse electric field is generated) is less than the channel length. In preferred embodiments the gap spacing is between 10 and 100 microns. Such an arrangement allows the generation of relatively large electric fields across the channel width with relatively low voltages and power consumption. In preferred embodiments of the invention, the electric fields may be large enough to cause ion fragmentation or ion cracking. This allows large ion species to be fragmented into smaller species, which can improve detector sensitivity and reduce the likelihood of interferents obscuring results.

The spectrometer preferably comprises means for heating the filter. Preferably the filter may be heated to at least 150° C. Heating the filter can improve performance, and will assist in removing contaminants from the filter. A separate heater may be provided (for example, a substrate on which the filter is mounted), although preferably the heating means is integrated with the filter. In preferred embodiments, the filter comprises a substrate which is heated, for example by Joule effect heating when a voltage is applied across the substrate. If the substrate is integrated into the filter, then such a voltage will be applied when the filter electrodes are actuated. The preferred microscale embodiments of the invention allow relatively low voltages to be used to provide effective heating by the Joule effect.

The spectrometer conveniently comprises a plurality of functional layers; each layer may have a wafer-like form. This arrangement is advantageous in assembling a micro machined spectrometer since it allows mass production (for example, batch or parallel manufacturing processes) semiconductor techniques to be used. The use of semiconductor techniques generally means that manufacture will take place in a clean room environment, such that lengthy decontamination and preparation steps are not needed before the assembled product can be used. Such a spectrometer will also be relatively compact due to the layer structure, which thus allows for greater miniaturization than otherwise. For example, each of the ionizer, filter, and detector may comprise a functional layer. In certain embodiments, it is possible to combine one or more functional layers on a single physical wafer-like layer. For instance, the filter layer and detector layer could be merged by using a silicon on insulator (SOI) wafer handle layer as the detector electrode and depositing the integrated circuitry on the backside, or simply moving the control electronics out of the device. The ionizer could be integrated with an inlet layer by patterning a metallic radio-isotope film on the underside of the inlet slab. In one embodiment, the sensor could be composed of just two layers: all integrated filter and detector layer fabricated in a single SOI wafer, and a porous inlet cap with metal ionization material patterned on the underside. This embodiment would require just one bonding step.

In embodiments the channels are substantially perpendicular to a face of the filter. Preferably the filter has face area to channel length ratio of greater than 1:1 (mm), more preferably greater than 10:1 or 100:1 (millimeters). For example a filter may have an 8 mm×8 mm face area and a channel length of approximately 200 µm.

The spectrometer may further comprise one or more of the following additional components; in preferred embodiments, each of these forms an additional functional layer: a) An inlet layer may be present, to prevent unwanted particles from entering the spectrometer while permitting analytes to diffuse into the device. The inlet layer is conveniently made from a porous material, such as a porous ceramic. b) A dehumidifier layer to deplete water vapor from the spectrometer. This layer may comprise an absorbent material; alternatively a desiccant or similar may be used. The layer may further include a heating element, which may be used to purge the absorbent material periodically. c) A preconcentrator layer, to accumulate and periodically release analyte to effectively concentrate the analyte. This layer may also comprise an absorbent material, such as a molecular sieve having pores of an appropriately large size to absorb the desired range of analytes. A heating element may then be activated to release absorbed analytes periodically. d) A dopant layer comprising a material imprecated with a desired chemical or dopant that is released or desorbed from the layer and into the active region to affect chemical reactions and therefore modify performance. This could be for example ammonia to enhance atmospheric pressure ionization of certain compounds or could be for example water, which is known to enhance separation of compounds in the spectrum and therefore resolution.

The detector may comprise an electrode located on a substrate. Conveniently the detector is a wafer-like semiconductor substrate; for example, silicon. The detector may further comprise control circuitry and the like; this is conveniently formed on the semiconductor substrate. The detector may further comprise connectors for connecting the control circuitry and/or the electrode to a processor means or the like for monitoring the electrode or controlling the device.

The spectrometer may also comprise means for generating a gas counterflow through the filter against the direction of movement of ions. Rarely will all of a sample be ionized, such that intact molecules or partial ionization products may enter the filter. Such molecules in the filter region may lead to further reactions and interactions, which cause deleterious effects such as peak shifting etc. The use of a gas counterflow can assist in removing contaminants from the filter, or in maintaining an unreactive environment within the filter. The gas used may be unreactive—for example, nitrogen or helium—or may be selected to affect affinity of contaminants to ionization—for example, ammonia, DCM etc may be used. A gas counterflow can also be used to alter mobility of ions within the filter. The gas counterflow may be at a very low flow rate; for example, a minimal pressure difference between sides of the filter is generally sufficient, since the flow is not needed to move ions (unlike gas flows in conventional ion spectrometers). Thus miniaturized pumps or diaphragms may be used, with relatively low power consumption; or a pressurized gas reservoir may be used.

According to a further aspect of the invention, there is provided a method of analyzing a sample, the method comprising the steps of: providing a first drive electric field along the length of an ion channel; providing a second transverse electric field orthogonal to the first; ionizing a sample to generate ions adjacent an entrance to the ion channel; and detecting generated ions which have passed through the ion channel.

Preferably the drive electric field is a static electric field; that is, the field does not vary over time. However a time-varying field can also be employed, as previously mentioned. The field may be generated by application of a DC bias across the electrodes.

The transverse electric field may vary over time, and may be generated by application of an AC voltage across the electrodes. In preferred embodiments of the invention, the transverse electric field comprises an AC component and a DC component. The DC component is preferably opposed to the AC component; that is, the AC component will tend to drive ions towards one side wall of the ion channel, while the DC component will tend to drive the ions towards the other side wall of the channel. Parameters may be varied as previously described.

The drive and transverse electric fields are preferably provided simultaneously. Preferably the drive and transverse electric fields are generated by a plurality of electrodes, each electrode contributing a component of both the drive and the transverse electric fields.

The method may also comprise the step of applying a counterflow of gas across the filter opposed to the direction of motion of the ions. The method may further comprise the step of fragmenting ions by application of a sufficiently large electric field across the ion channel. The ion channel may be heated, for example by applying sufficient voltage across a substrate to generate Joule heating.

according to a further aspect of the present invention, there is provided an ion filter for use in a spectrometer such as an ion mobility spectrometer, the filter defining at least one ion channel along which ions may pass, and a plurality of electrodes disposed proximate the ion channel, the electrodes being configured to allow generation of a first drive electric field along the length of the ion channel, and generation of a second transverse electric field orthogonal to the first, wherein each of said plurality of electrodes is involved in generating a component of both the drive and the transverse electric fields.

At least two electrode pairs may be provided; one electrode is conveniently situated at each corner of the channel. The electrode pairs are transversely separated by the channel itself, while the pairs may be vertically separated by an insulating material to provide structural stability. Preferably four electrodes are provided at each ion channel.

The filter preferably comprises a plurality of ion channels, and conveniently more than 5, more than 10, more than 15, and more than 20 ion channels. The channels may conveniently be defined by a plurality of electrode fingers forming a comb-like arrangement. In preferred embodiments, the filter comprises two or more interdigitated electrode arrays, each array having a plurality of electrode fingers, optionally curved as previously described.

Preferably the ion channels are elongate; that is, they have a relatively short length (the direction along which ions will flow) and a relatively short width (in a minor transverse direction), with a relatively long depth (in a major transverse direction).

The filter preferably comprises a resistive substrate on which is disposed a conductive surface to form an electrode. A conductive surface may be disposed on two faces of the resistive substrate. The substrate may comprise silicon. The conductive surface may comprise metal, polysilicon or the like. In preferred embodiments, where the spectrometer is on a micro machined scale, the substrate and surface may conveniently be etched to form a desired shape and configuration, and to provide the ion channels, using conventional semiconductor processing techniques. This allows many channels to be formed in parallel, and on a small scale.

Preferably the length of the ion channel is less than the depth of the filter, and preferably significantly less; for example, at least 10 times less. In some preferred embodiments, the filter has a generally wafer-like form, with the channel length being a fraction of the filter depth. In a particularly preferred embodiment, the channel length is less than 1000 microns, less than 900 microns, and less than 800 microns, while the filter depth is more than 10,000 microns. Preferred channel lengths are from 1000 to 100 microns, more preferably 800 to 300 microns, and most preferably 500 to 300 microns.

According to a further aspect of the present invention, there is provided an ion mobility spectrometer comprising an ionizer, an ion filter, and an ion detector; wherein the ion filter defines a plurality of ion channels along which ions may pass from the ionizer to the ion detector; and wherein the ion filter comprises a plurality of electrodes disposed proximate the ion channel; the spectrometer further comprising electrode control means for controlling the electrodes such that a first drive electric field is generated along the length of the ion channel, and a second transverse electric field is generated orthogonal to the first.

The invention also provides an ion filter for use in a spectrometer such as an ion mobility spectrometer, the filter defining a plurality of ion channels along which ions may pass, and a plurality of electrodes disposed proximate the ion channel, the electrodes being configured to allow generation of a first drive electric field along the length of the ion channel, and generation of a second transverse electric field orthogonal to the first.

According to a still further aspect of the present invention, there is provided a method of manufacturing an ion mobility spectrometer, the method comprising the steps of: providing a generally planar resistive substrate having a conductive layer provided on two faces thereof; patterning, for example etching the substrate to provide a filter comprising two or more interdigitated electrode arrays defining a plurality of ion channels having electrodes disposed proximate said channels; bonding said filter on one face to a generally planar ion detector layer comprising a detector electrode; and attaching, for example bonding said filter on the opposed face to a generally planar ionization layer comprising means for ionizing an analyte.

Preferably the method further comprises the step of providing electrode control means for controlling the electrodes such that a first drive electric field is generated along the length of the ion channel, and a second transverse electric field is generated orthogonal to the first.

BRIEF DESCRIPTION OF THE DRAWINGS

These and other aspects of the present invention will now be described by way of example only with reference to the accompanying Figures, in which:

FIG. 1 is a schematic of a conventional FAIMS filter structure;

DETAILED DESCRIPTION

FIG. 1 shows in a schematic form the operation of conventional FAIMS (field asymmetric ion mobility spectroscopy). Air is drawn at atmospheric pressure into a reaction region where the constituents of the sample are ionized. The ions 12a, 12b are blown between two metal electrodes 14a, 14b, one with a low-voltage DC bias and the other with a periodic high-voltage pulse waveform, to a detector plate (not shown) where they collide and a current is registered. Ions are quickly driven toward one electrode during the pulse phase and slowly driven toward the opposite electrode between pulses. Some ions 12a impact an electrode before reaching the detector plate; other ions 12b with the appropriate differential mobility reach the end, making this a differential mobility ion filter. A plot of the current generated versus DC bias provides a characteristic differential ion mobility spectrum. The intensity of the peaks in the spectrum, which corresponds to the amount of charge, indicates the relative concentration of the agent.

Figure 2A:
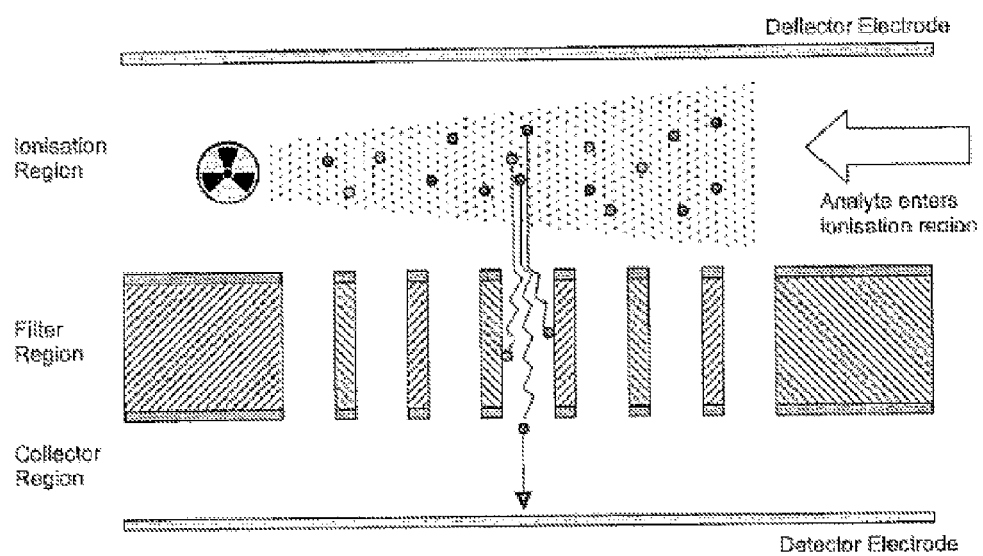
FIG. 2 is a schematic of a FAIMS filter structure as may be used with a spectrometer in accordance with embodiments of the present invention.
Figure 2B:
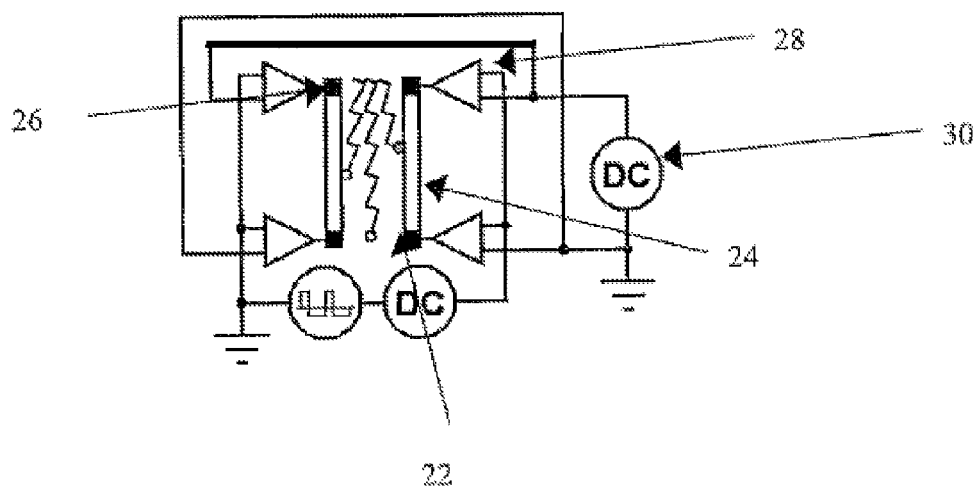

A schematic diagram of the operation of the filter in accordance with the present invention is shown in FIGS. 2a and 2b. This design is intended to overcome or to reduce scaling limitations. The disclosed approach includes an innovative electrode geometry affording low voltage operation. An interdigitated electrode structure is formed by etching a dense array of narrow channels through high resistivity silicon. Ions are driven through the channels via a novel transport mechanism relying on electric fields instead of moving gas flows to achieve pumpless operation. Ion channels 22 are defined by the silicon substrate 24 which carries a conductive layer 26, defining electrodes at each corner of the entrance and exit from the ion channel. The amplifiers 28 depicted represent analogue adders. Note that the metal plates are replaced by high resistivity silicon. In addition to the high-voltage pulse and low voltage DC bias generated across the channel, a further DC source 30 creates a drive electric field to drive ions through the channel, eliminating the need for a moving gas flow. A theoretical analysis has shown that ions can be propelled fast enough to avoid ion loss into channel walls due to diffusion. FIG. 2a shows a preferred embodiment having multiple ion channels, while FIG. 2b illustrates a single ion channel for clarity, together with the controlling electronics. The filter is typically operated with an electric field of 40 to 200 V across the channel, with the high-voltage pulse being typically from 3 MHz to 10 or 20 MHz. The drive field may generally be from 10 to 40V.

Figure 3:
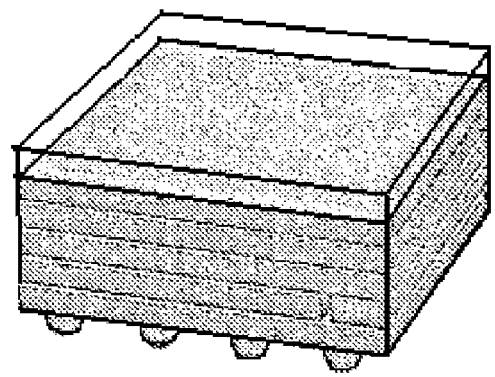
FIG. 3 is a perspective view of a spectrometer in accordance with an embodiment of the present invention.

FIG. 3 shows a perspective view of an exemplary sensor made in accordance with the present invention. The sensor is formed from a number of separate layers bonded together, as will be described. The ion channels are oriented vertically so that ion movement is directed perpendicular to the silicon substrate surface. This geometry permits subsystems to be segregated to separate wafer layers that are stacked and bonded in the order of ion flow, producing a fully integrated gas sensor with the smallest possible size.

Figure 4:
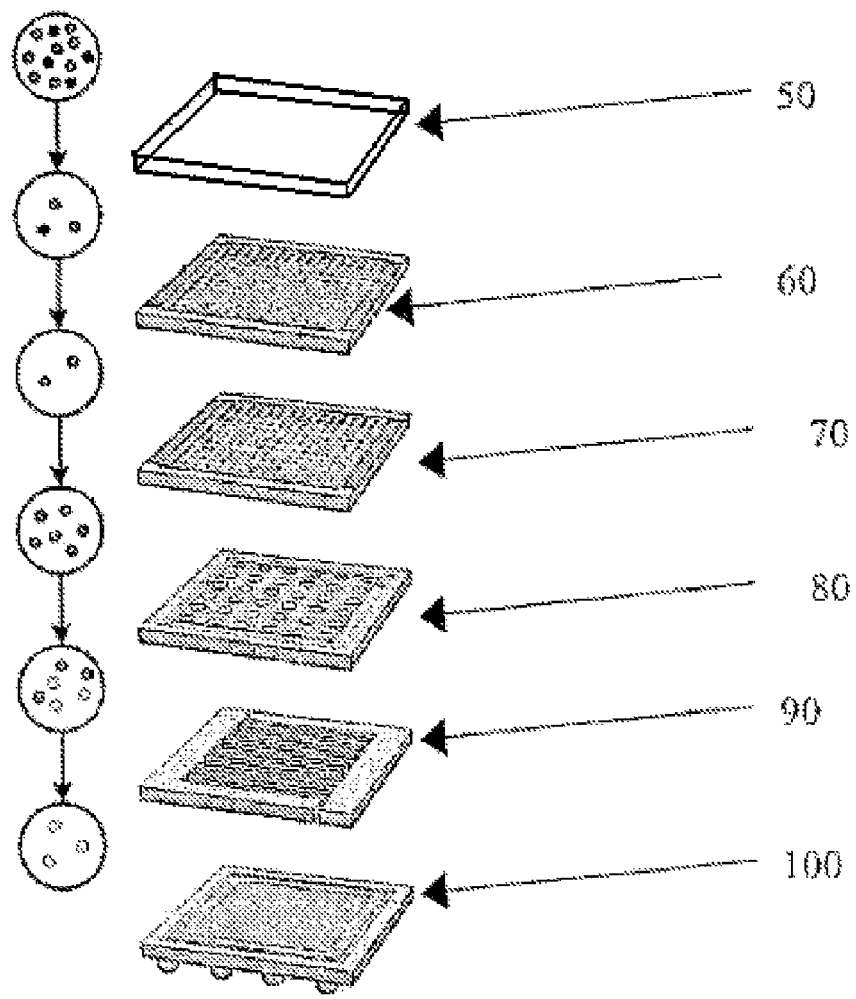
FIG. 4 is an exploded perspective view of the spectrometer of FIG. 3.

An exploded perspective view of the sensor is shown in FIG. 4. The spectrometer includes a number of layers in addition to the filter layer. From top to bottom, these layers are: an inlet layer 50, dehumidifier layer 60, preconcentrator layer 70, ionizer layer 80, filter layer 90, and detector layer 100.

This is only one embodiment envisioned and could be greatly simplified or otherwise modified in a variety of ways. For instance, the filter layer and detector layer could be merged by using the silicon on insulator (SOI) wafer handle layer as the detector electrode and depositing the integrated circuitry on the backside, or simply moving the control electronics out of the device. The dehumidifier and preconcentrator layers could be integrated together on the same layer, or moved outside of the device and into the cavity housing the sensor. The ionizer could be integrated with the inlet layer by patterning a metallic radioisotope film on the underside of the inlet slab. In the simplest case, the sensor could be composed of just two layers: an integrated filter and detector layer fabricated in a single SOI wafer, and a porous inlet cap with metal ionization material patterned on the underside. This embodiment would require just one bonding step.

Our concept excels by harnessing small size properties for improved performance. The microstructured filter layer uses low voltages and implements a novel method of analyte transport, which eliminates the need for moving gas flows and allows pumpless operation. Microscale thermal isolation facilitates low power operation of a fast microscale preconcentrator. A closely integrated detector improves sensitivity. The small size of the sensor cavity allows a simple approach for removing performance degrading humidity. The batch fabrication advantages of our micro-electro-mechanical-system (MEMS) implementation make it well suited for ubiquitous deployment scenarios.

Construction

The completed sensor is formed by bonding separate subsystem layers together as shown in FIG. 4. This construction allows each subsystem to be fabricated on an independent wafer for simplified development and ease of production. Details of the function and fabrication of each subsystem layer is given below. The layers are electrically interconnected using through-chip vias or simple wire-bonding.

Figure 5:
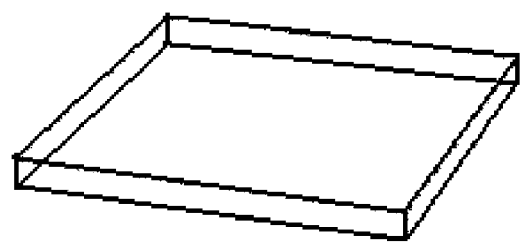
FIG. 5 is a perspective view of the inlet layer of the spectrometer of FIG. 3.

FIG. 5: Inlet Layer

Function: The function of this layer is to prevent particles from entering the detector while permitting analytes to diffuse through to the analysis region.

Construction: This layer is made of a micro-porous medium (such as ceramic) with a pore size small enough to prevent particulates from passing through. It has a simple planar construction as shown.

Fabrication: The micro-porous medium is received as appropriately sized wafers requiring no further fabrication. It is simply bonded to the top of the sensor wafer stack.

Figure 6:
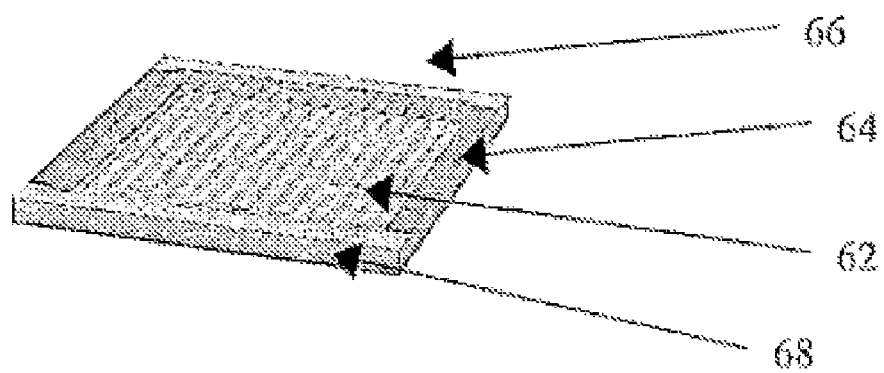
FIG. 6 is a perspective view of the dehumidifier layer of the spectrometer of FIG. 3.

FIG. 6: Dehumidifier Layer

Function: The function of this layer in to control the humidity of the sensor cavity. Water vapor affects separation of compounds in FAIMS, and although it can help to increase resolution if it is not controlled it can add uncertainty to the measurements that leads to poor performance. Humidity control is achieved by removing the water vapor or drying the sensor cavity. Drying is accomplished using a material that selectively removes humidity at the sensor entrance before it can enter the analysis region. This material is periodically heated to purge absorbed moisture.

Construction: A special absorbent film 62 covers a micro hot plate 64 suspended along the top surface of this section. The micro hot plate consists of a meandering polysilicon wire deposited onto a silicon nitride membrane 66. The components are all formed on a silicon substrate 68. The absorbent film contains a molecular sieve compound with pores 3 angstroms across or less. The pores are just large enough to absorb water molecules but too small to absorb analyte compounds.

Fabrication: Polysilicon and silicon nitride depositions are performed and lithography is used to pattern the micro hot plate. Alternatively, a commercial CMOS process is used. An absorbent film is then deposited on top and an etch release is employed to suspended the structure.

Figure 7:
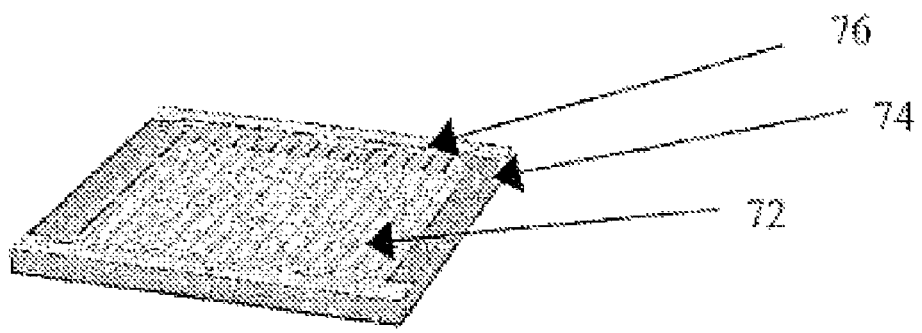
FIG. 7 is a perspective view of the preconcentrator layer of the spectrometer of FIG. 3.

FIG. 7: Preconcentrator Layer

Function: The function of this layer is to concentrate the analyte for analysis. This is accomplished using a molecular sieve material 72 like that used in the dehumidifier layer, but which is less selective. It is heated to release a concentrated analyte plume during the analysis period.

Construction: A special absorbent film 72 covers a micro hot plate 74 suspended along the top surface of this section. The micro hot plate consists of a meandering polysilicon wire deposited onto a silicon nitride membrane 76. The absorbent film contains a molecular sieve compound with a large pore size, which is selected so that all of the desired analytes are absorbed.

Fabrication: Polysilicon and silicon nitride depositions are performed and lithography is used to pattern the micro hot plate. Alternatively, a commercial CMOS process is used. An absorbent film is then deposited on top and an etch release is employed to suspended the structure.

Figure 8:
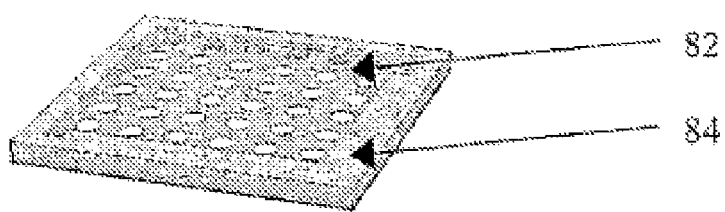
FIG. 8 is a perspective view of the ionizer layer of the spectrometer of FIG. 3.

FIG. 8: Ionizer Layer

Function: The function of the ionization layer is to ionize the analyte. A radioisotope is initially used for this purpose, but an ultraviolet light emitting diode (UV-LED) can be used. Irradiation is confined completely within the ionization assembly so that no ionization occurs within the filter region, which would degrade sensor performance.

Construction: This layer is essentially a hollow cavity in which ionization takes place. An UV-LED or radioactive foil 82 is attached to provide the ionization stimulus. UW-LEDs are more desirable, as they are safer to process, are potentially more selective, can be cycled off, and raise less alarm among the public. Radioactive sources consume no power and can be safe. An acceptable ultraviolet source preferably emits wavelengths shorter than 280 nm.

Fabrication: A silicon nitride membrane 84 is deposited and a metal seed layer is deposited on top. Openings are patterned through both. The radiation source 82 is then electroplated onto the seed layer. Finally, a bulk etch is performed to make the cavity.

Figure 9:
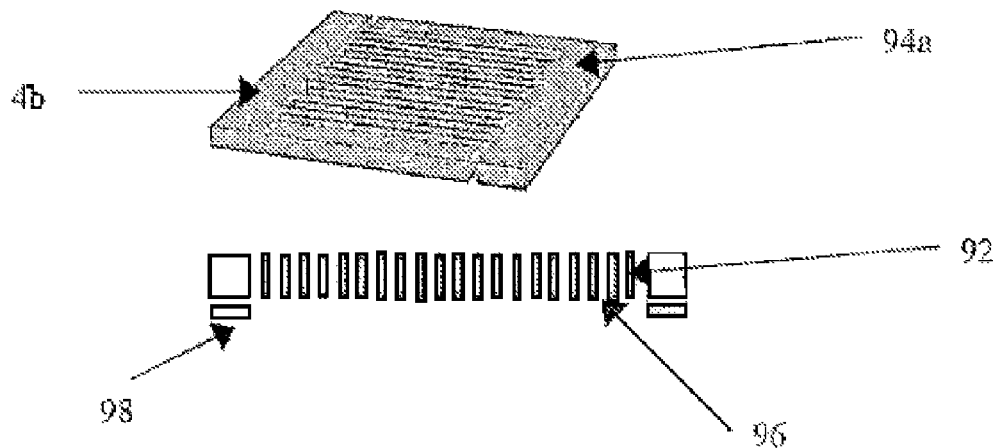
FIG. 9 is a perspective view of the filter layer of the spectrometer of FIG. 3.

FIG. 9: Filter Layer

Function: The function of the filter layer is to admit selected ionic species to the detector and neutralize all unselected species. This is accomplished by introducing the ionized analyte into an array of microchannels 92 where two orthogonal electric fields act simultaneously on it. A drive electrostatic field is applied to propel ions quickly through the filter region before they have time to diffuse into the microchannel walls. A transverse oscillating electric field is applied to select species with a particular ratio of high field mobility to low field mobility.

Construction: This layer consists of a pair of interdigitated electrodes 94a, 94b slightly spaced apart. The electrodes are fabricated out of high resistivity silicon 96 with features a few microns wide and several hundred microns deep, creating many (typically tens to hundreds) high aspect ratio channels 92 in which the filter action takes place. Most of the volume occupied by the filter layer is open space. The large combined aperture of the channels means that ions can be efficiently coupled into the filter region so that ion throughput, and hence device sensitivity, can be made very high. The narrow channel width means that the voltages needed to create transverse fields are very small, typically tens of volts, since voltage scales with gap distance. High resistivity silicon is used so that the electrodes act as resistors. Currents passing from top to bottom through each electrode generate the drive electrostatic field used to drive ions through the structure.

Fabrication: The filter layer is fabricated using largely conventional micronmachining techniques. Silicon on insulator (SOI) wafers are custom made with a high resistivity device layer specially doped on both sides to form the thin conductive electrode surfaces 96 and facilitate ohmic contacts 98. Deep reactive ion etching (DRIE) is used to create the high aspect ratio features. Calculations show that a 20:1 aspect ratio is sufficient; other aspect ratios may of course be used, for example 10:1 or greater than 20:1. A back etch and then an oxide etch release are performed to open the channels and provide access to covered electrode surfaces.

The filter structure can be manufactured by a range of conventional microfabrication techniques. One representative process involves the following steps. The substrate used is a high resistivity silicon wafer. Aluminum is deposited on tie top and bottom faces of the wafer, followed by a photo resistant coating on each face. The top face is masked and subjected to photolithography, after which the aluminum coating of the top face is wet etched to provide an array of electrodes. The photoresist is stripped from both faces, and the process repeated to form the bottom face electrodes. A further resist coating is applied to the top face, after which the silicon is etched from the lower face using deep reactive ion etching to form channels. The photoresist is stripped for the final time, and the filter is ready for further processing.

In a variation of this technique, the silicon wafer may be initially bonded on the bottom face to a glass substrate; the various etching steps are then carried out from the top face to create channels and electrodes, after which the glass substrate is acid etched to expose the bottom face of the wafer, leaving a glass support in contact with the wafer. Other variations may include the use of substrates other than glass; and performing the steps listed in a different order.

Figure 13:
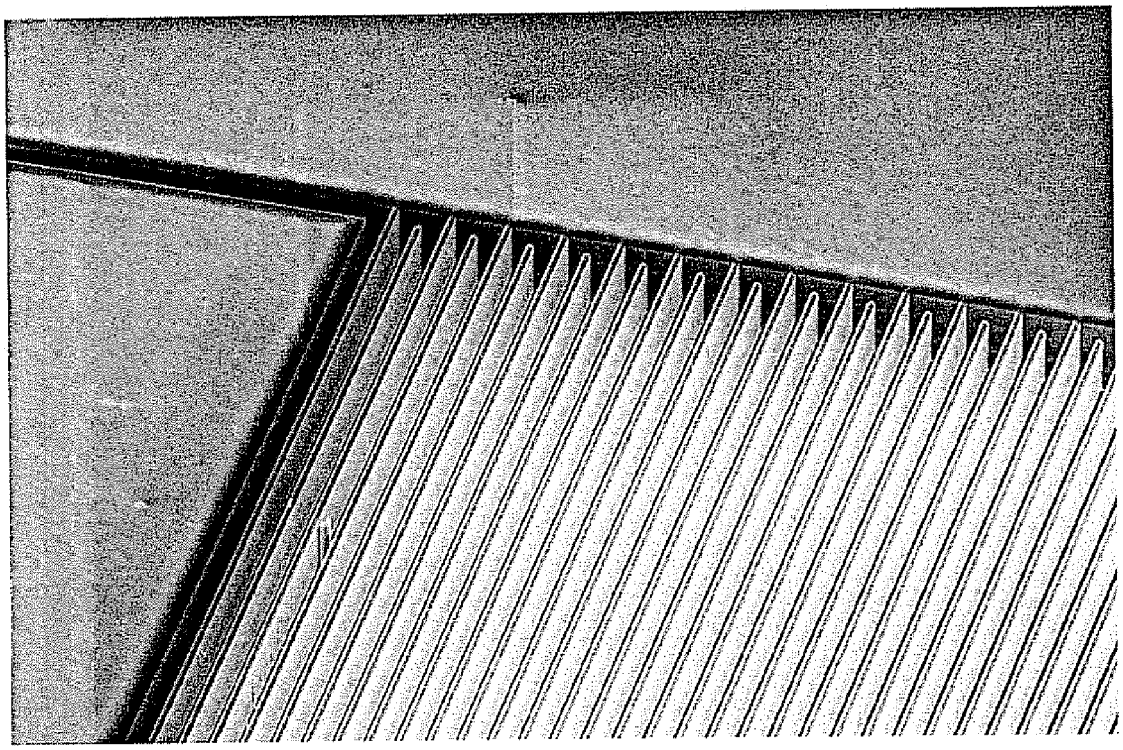
FIG. 13 is an electron micrograph of a portion of an ion filter in accordance with an embodiment of the present invention, illustrating the filter structure.

FIG. 13 shows an electron micrograph of a portion of a filter structure made in accordance with the present invention.

Figure 10:
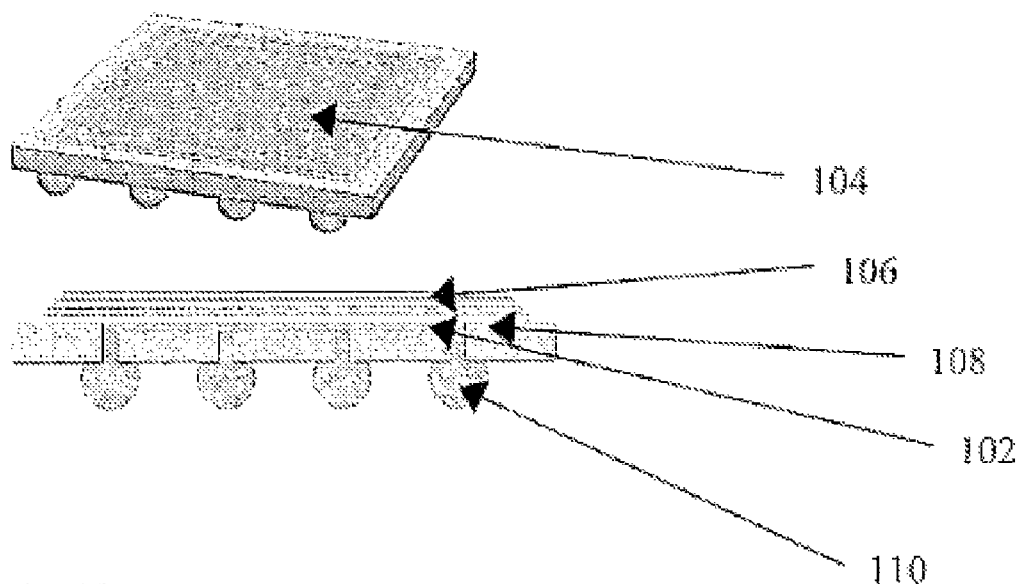
FIG. 10 is a perspective view of the detector layer of the spectrometer of FIG. 3.

FIG. 10: Detector Layer

Function: The functions of the detector layer are to generate the signals that drive the ion filter layer, collect and measure the current of filtered ion species, and output spectrometry data calculated by correlating detected current with drive signals.

Construction: All system circuitry 102 is included in this layer, namely: filter electrode drivers, detector transimpedance amplifier, data converters, and control logic. The circuitry is protected by an oxide layer 106 and the ion collector electrode 104 is exposed on top. To provide better passivation, an intermediate metal layer 108 may be added to guard the collector electrode from leakage currents. Vias from the circuitry to solder pads 110 on the bottom of the substrate provide for flip-chip mounting. Multiple detector channels may be employed to decrease analysis time. This scheme requires that the filter electrode and associated circuitry be replicated in parallel.

Fabrication: All circuitry and electrodes are fabricated using a commercial mixed-signal BiCMOS process capable of the voltages required. The delivered wafer is post-processed using DRIE and metallization steps to form vias between the circuitry and backside and is then solder bumped.

In certain embodiments the detector electrode may be integrated into the filter layer; for example, by bonding or fabricating the filter layer on a substrate which acts as a detector electrode.

Control and Analysis Algorithms

Because the filter layer electrodes are controlled using low voltages and conventional integrated circuitry, the electric field strength within the filter region can be controlled more precisely and in more complicated ways than possible with conventional designs. The differential mobility can thus be determined more precisely and, hence, the resolution is expected to improve due to this precision. More complicated control and analysis algorithms may allow lower false alarm rates by sampling analyte ion mobilities at multiple field strengths, instead of at just two points, as is the case with existing FAIMS designs.

The assembled spectrometer may be connected to a processor means, such as a computer or the like, which may be used to control the spectrometer and to monitor data.

Figure 11:
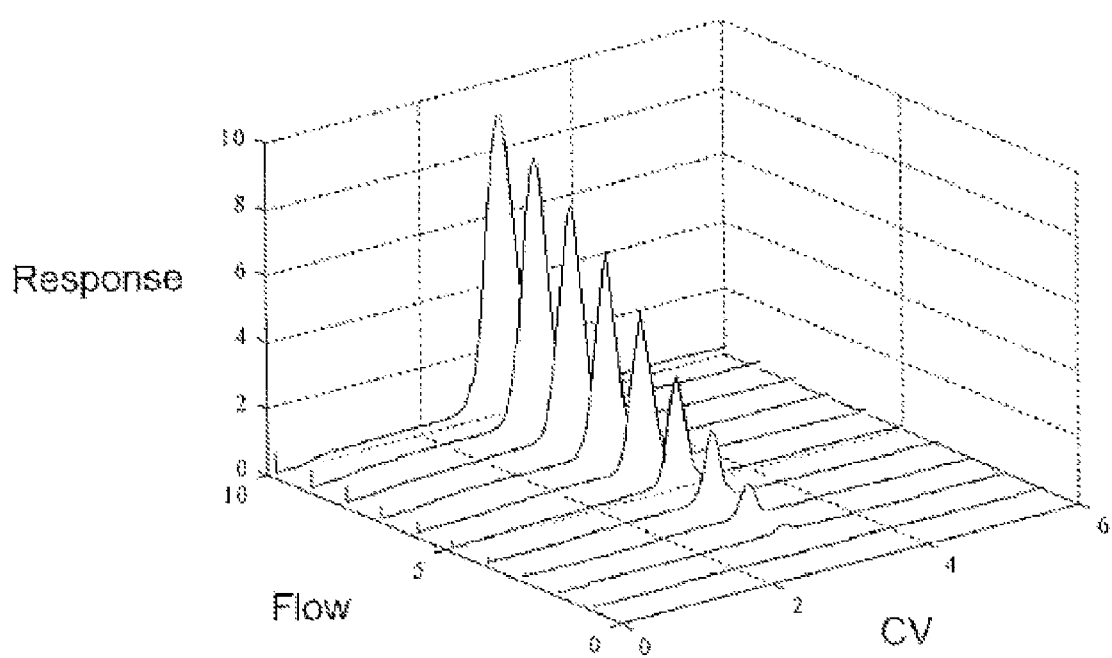
FIG. 11 is a graph showing the response of a spectrometer according to the invention as sample flow is varied.
Figure 12:
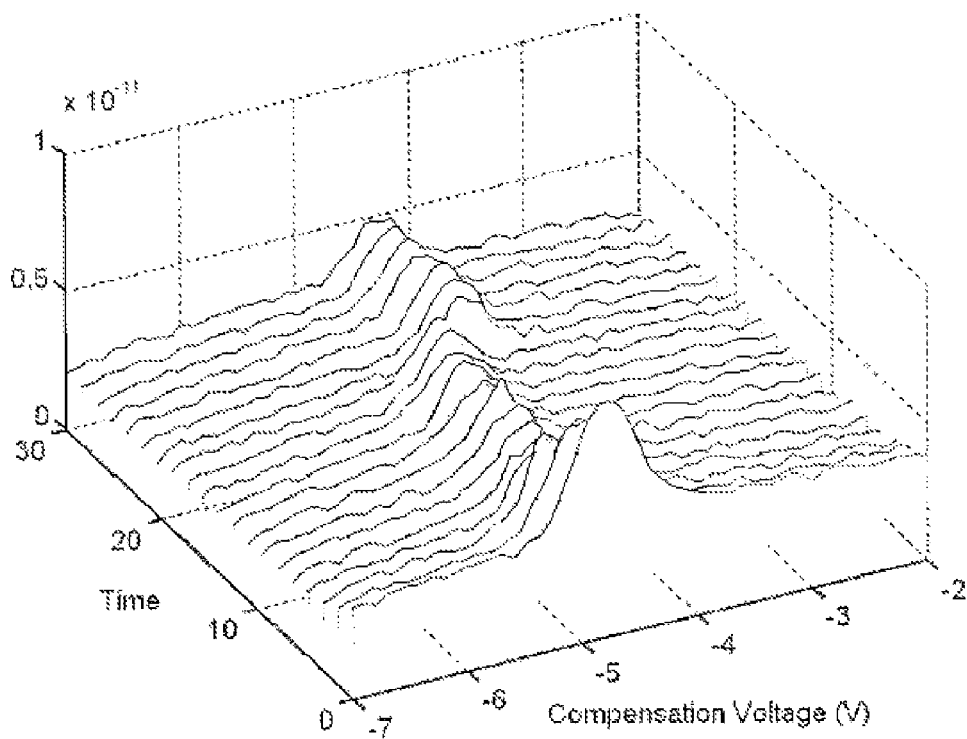
FIG. 12 is a graph showing the response of a spectrometer according to the invention to acetone as an analyte.

A sample device was constructed as described, and used to monitor a test sample of acetone. FIG. 11 is a graph indicating the varying response of the device as the flow of acetone over the device is increased. FIG. 12 shows the shift in response from the device as acetone is introduced into the device, indicating that a sensitive response can be obtained.

Embodiments of spectrometers in accordance with the present invention may have a number of benefits of the design compared with conventional spectrometers. These include:

a) Tight integration and small sensor size. The end product is a fully integrated monolithic sensor which can be produced with a footprint under one square centimeter and a volume less than one cubic centimeter. Its miniature size can be expected to make many new applications and deployment scenarios possible, and its monolithic construction will make it resilient against high forces.

b) Simplified system design, modification, fabrication, and verification. The present approach slices the three dimensional sensor into separate two dimensional layers. These layers are designed independently and in parallel. They can be fabricated using existing micromachining processes and easily tested using conventional wafer probe equipment.

c) Reduces or eliminates need for additional packaging and assembly. Because subsections are connected in a gas tight manner by wafer bonding, little or no external packaging is required. The pumpless design eliminates the need for post-fabrication assembly with an external pump. MEMS packaging can be a significant component of total device cost. Designs with simplified packaging requirements are thus favorable.

d) Flip-chip implementation. Ions are drawn in through the top and directed to the detector at the bottom. Because the detector layer includes all circuitry and is the very bottom layer, through-chip vias can connect the circuitry with solder pads on the back side to form a flip-chip device. A flip-chip connection scheme requires the smallest board real estate for mounting, offers the lowest possible weight, and has the most reliable interconnects.

e) Manufactured using conventional microfabrication technology. Only standard micromachining techniques, such as DRIE of SOI, are required. Thus, minimum process development is required, base materials are readily available in volume at economical prices, and fabs capable of commercial production already exist.

In certain embodiments of the invention, the spectrometer may further comprise a membrane, and in particular a semipermeable membrane. For example, the membrane may be made from expanded PTFE (such as that sold under the name GORE-TEX®), or from dimethlylsilicone. Such semi-permeable membranes may find many uses in the invention.

The inlet of the spectrometer may be covered by a membrane. This has a number of functions; one is to prevent dust and particulates from entering the device, while the semipermeable membrane still permits gaseous analytes to enter. The membrane may exclude polar molecules from the active region of the spectrometer; excessive polar molecules can lead to clustering which reduces resolution of the device and affects the data. The membrane serves to concentrate analytes in the region immediately adjacent the sensor, so improving sensitivity. Further, liquids may be passed over the membrane, such that the analyte can diffuse from the liquid into the device in gas phase, thereby permitting analysis of liquid samples. The membrane may incorporate a heating element; varying the temperature of the membrane can affect diffusion processes across the membrane so allowing additional selectivity.

Selection of appropriate membrane material may also be used to exclude particular molecular species from the device.

Figure 14:
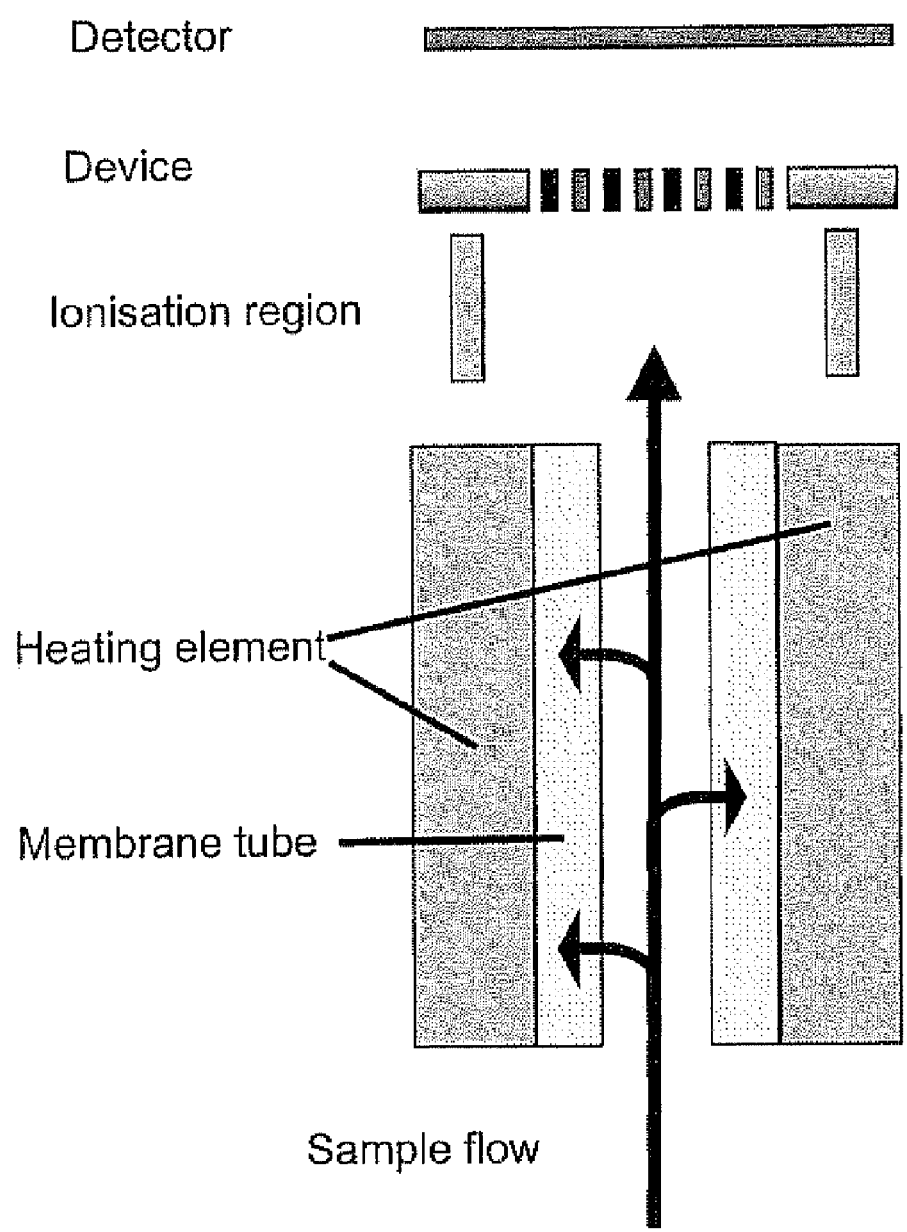
FIG. 14 shows the use of a heated membrane inlet tube in accordance with the present invention.
Figure 15:
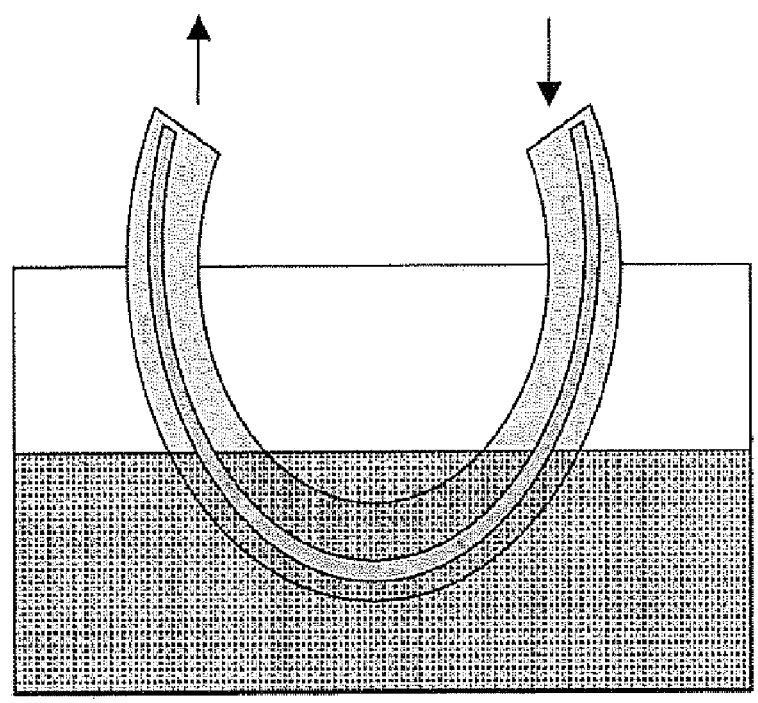
FIG. 15 shows the use of an inlet tube to sample fluids in accordance with the present invention.

A membrane may also be used as a pre-concentrator; particularly if the membrane also incorporates a heating element. Analytes may diffuse into the membrane where they will be held until the temperature is raised; this releases a relatively high concentration of analyte into the device. The membrane may simply cover the inlet of the spectrometer, but in preferred embodiments may take the form of an inlet tube leading to the device; sample may be continuously passed along the tube giving some sample data over time, while a concentrated plug of analyte may be released when desired from the inlet tube. For sampling liquids, an inlet tube may be immersed in the sample, allowing analyte to diffuse from the liquid into the membrane. Heating of the membrane releases analyte into the spectrometer. Examples of these are shown in FIGS. 14 and 15.

A separate membrane may also be used as a sample introduction device. A PDMS (polydimethylsilicone) membrane (or other suitable material) containing an embedded silicon wafer can be introduced into a liquid or gaseous sample. Analyte from the sample is adsorbed into the membrane. The sample introduction device is then located adjacent the spectrometer, and a current passed through the silicon wafer, serving to heat the wafer and hence the membrane. Adsorbed analyte is then desorbed adjacent the spectrometer. This arrangement allows sampling to take place at a location remote from the spectrometer. The sampling device may be connectable to the electronics of the spectrometer to permit current to be passed through the silicon wafer.

Figure 16:
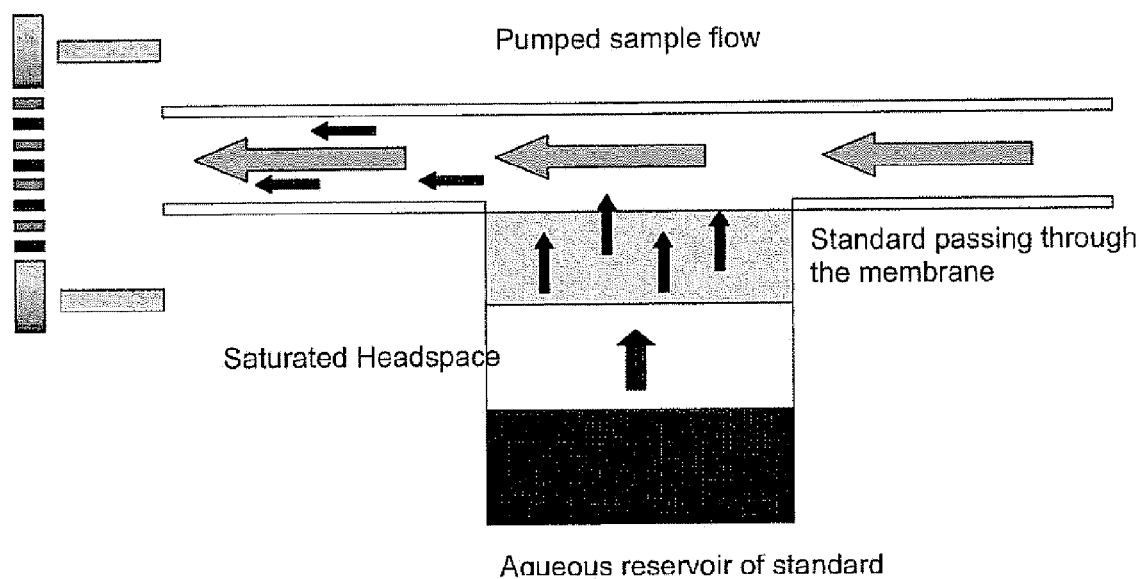
FIG. 16 shows the incorporation of a standard into an embodiment of the present invention.

Various membrane-related devices may be used to incorporate standards into the spectrometer. The use of standards can allow calibration of the spectrometer response, and in some circumstances can also correct for temperature or humidity variations. A membrane standard will release analyte at a generally constant rate dependent largely on the physical properties of the membrane chosen, rather than on the concentration of the standard itself. Such standards are therefore relatively simple to manufactures robust, and can be recharged without requiring accurate recalibration. Loading of the membrane standards may be achieved in numerous ways. For solids, the standards may be introduced during the membrane curing process. For liquids or gases the membrane may be used to enclose a sample of the standard; and for gases the membrane can be impregnated and stored in a controlled headspace. The membrane standard may be a separate component from the spectrometer, or may be incorporated internally into the spectrometer to allow ready calibration; for example, a standard may be connected to an inlet pipe leading to the spectrometer; this is illustrated in FIG. 16. An internal standard may also be used for continual monitoring and validation of sampling data. The standards used will depend on the particular application, but preferred standards will have a high proton/electron affinity or can donate protons/electrons; can be separated from target compounds; and will not be masked by naturally occurring interferents.

Multiple filters and/or detectors may be combined in a detector array to improve sensitivity to a range of analytes. With a single filter, it is necessary to sweep the compensation voltage to tune the filter to transmit certain ion species; for a large proportion of the time the compensation voltage may not be tuned to the analyte of interest, and there is a delay time as the voltage is swept. Combination of several filters and/or detectors allows each filter to remain tuned to a single voltage to detect a specific analyte of interest, while the array format allows detection of a range of different analytes. The output from the sensor array would be a discrete spectrum with a number of channels, corresponding to the number of analytes of interest. It is also possible to have several filters tuned to tie same voltage but with different dopant chemistries in each device to improve screening and reduce interference effects; or even several identical filters for redundancy.

Figure 17:
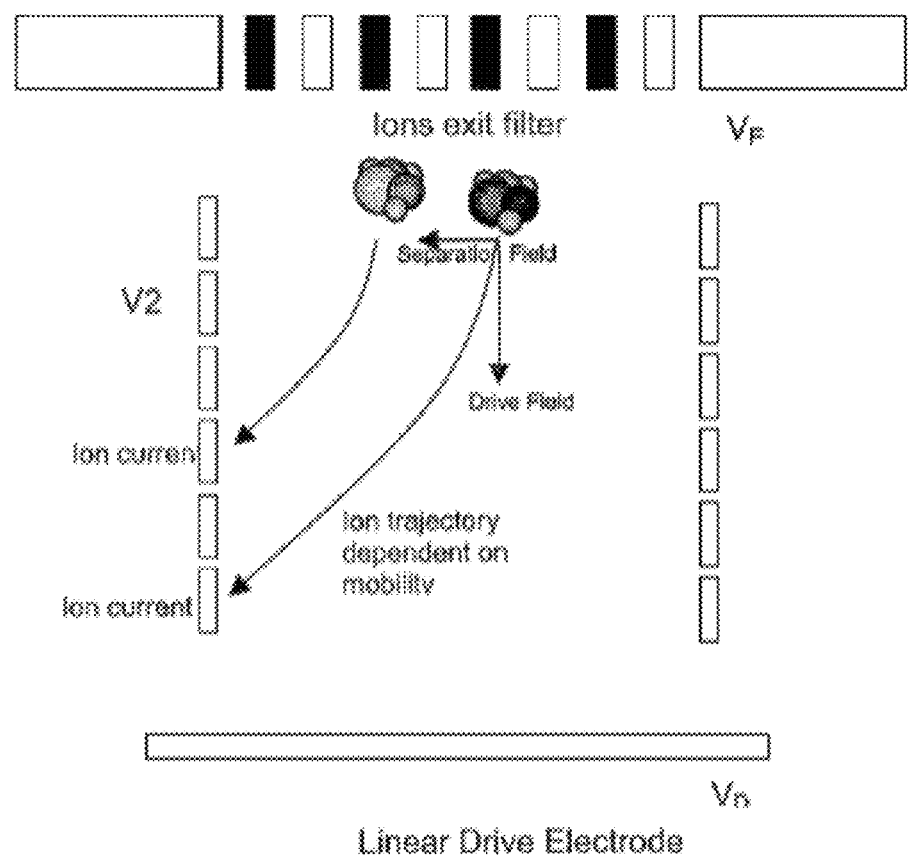
FIG. 17 shows a detector electrode array as may be used with embodiments of the present invention.

Further improvements in sensitivity can be achieved by using multiple detector electrodes with a single filter. When a single detector electrode is used, this is a single plate which measures the total ion current which may contain several ion types, while only a single type may be of interest. A series of discrete detector electrodes may be used, orthogonal to the exit path taken by the ions as they leave the filter; this creates all orthogonal field drawing the ions toward the detectors. The speed at which the ions move toward the electrodes is dependent upon the mobility of the ion; and as there is still a linear component to the electric field, ions of differing mobilities will strike different detector electrodes. This permits greater sensitivity in detecting different ion species which pass the filter. An example detector electrode array is shown in FIG. 17.

Another means whereby detector sensitivity may be improved is by coupling the detector electrode to a capacitor which gradually builds up charge as individual ions strike the detector plate. Periodic discharge of the capacitor allows the ion contributions to be summed over time, thereby increasing sensitivity and signal to noise ratio of the device.

Figure 18:
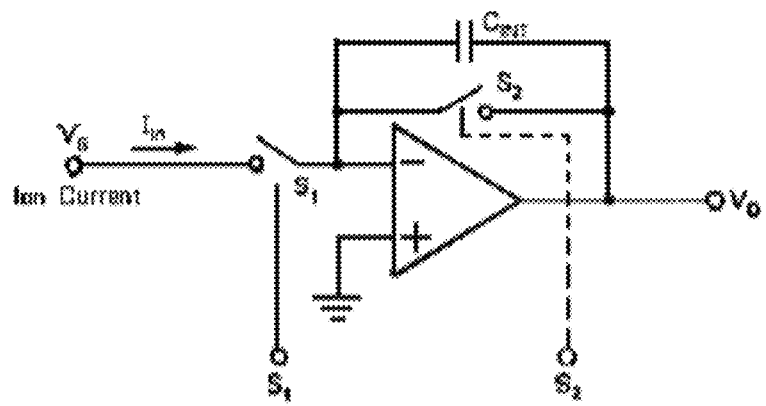
FIG. 18 shows a switched integrator which may be used with embodiments of the invention.

A switched integrator may also or instead be used to improve sensitivity in certain circumstances. The ion detector is connected by a switch to an integrator; this is switched to measure output voltage, and a second switch is cycled to reset the device. An example of a switched integrator is shown in FIG. 18.

In certain embodiments, the spectrometer of the present invention may be operated in a switch mode for detection; that is, the detector is activated periodically to take a sample at regular intervals. This operating mode may be used to moderate power consumption and to prolong operating life of the device. This is particularly of benefit when a device is intended to be used for prolonged monitoring of a sample; for example, in security applications or the like.

Operation of the spectrometer could also include varying the temperature and/or pressure at which the device is run, to vary the performance of the device.

Although embodiments of the invention thus far have been described in terms of using only an electric field to drive ions through the filter, it will be apparent that it is possible to use the filter in combination with a gas flow, either a counterflow as previously described, or as a flow in the same direction as the ion flow driven by the electric field.

A gas flow may be used in embodiments solely for introduction of ions into the spectrometer, while the electric field operates once the ions have entered the device.

Alternatively, the filter may be operated with only a transverse electric field to selectively admit ions; longitudinal movement of the ions is controlled purely by a longitudinal gas flow.

In some embodiments of the invention, the filter structure may be fabricated as completely solid metal elements, for operating in gas flow mode, or as a metal coated silicon or other wafer structure. Metal coating may be formed by, for example, sputtering, evaporation, electroplating, electroless electroplating, atomic layer deposition, or chemical vapor deposition. A solid metal device may be produced by water cutting, laser cutting, machining, milling, or LIGA. Although this arrangement does not have the advantages of a purely electric field driven device, the ability to make use of a miniaturized filter with a gas flow propulsion has advantages such as reducing the operating voltage. Use of an interdigitated array of ion channels compensates to some extent for the lower voltage used.

As mentioned above, gas flow may be used to couple ions into the spectrometer. An alternative introduction method is to use electrospray ionization. An analyte dissolved in solvent is forced through a capillary thin needle point which is charged. This induces a charge on the expelled droplets which are accelerated towards an oppositely charged pinhole orifice. This allows the use of a non-radioactive ionizer, as well as permitting liquid phase ionization without heating, which could degrade some analytes, and also permits the ionization of some macromolecules such as peptides.

Figure 19:
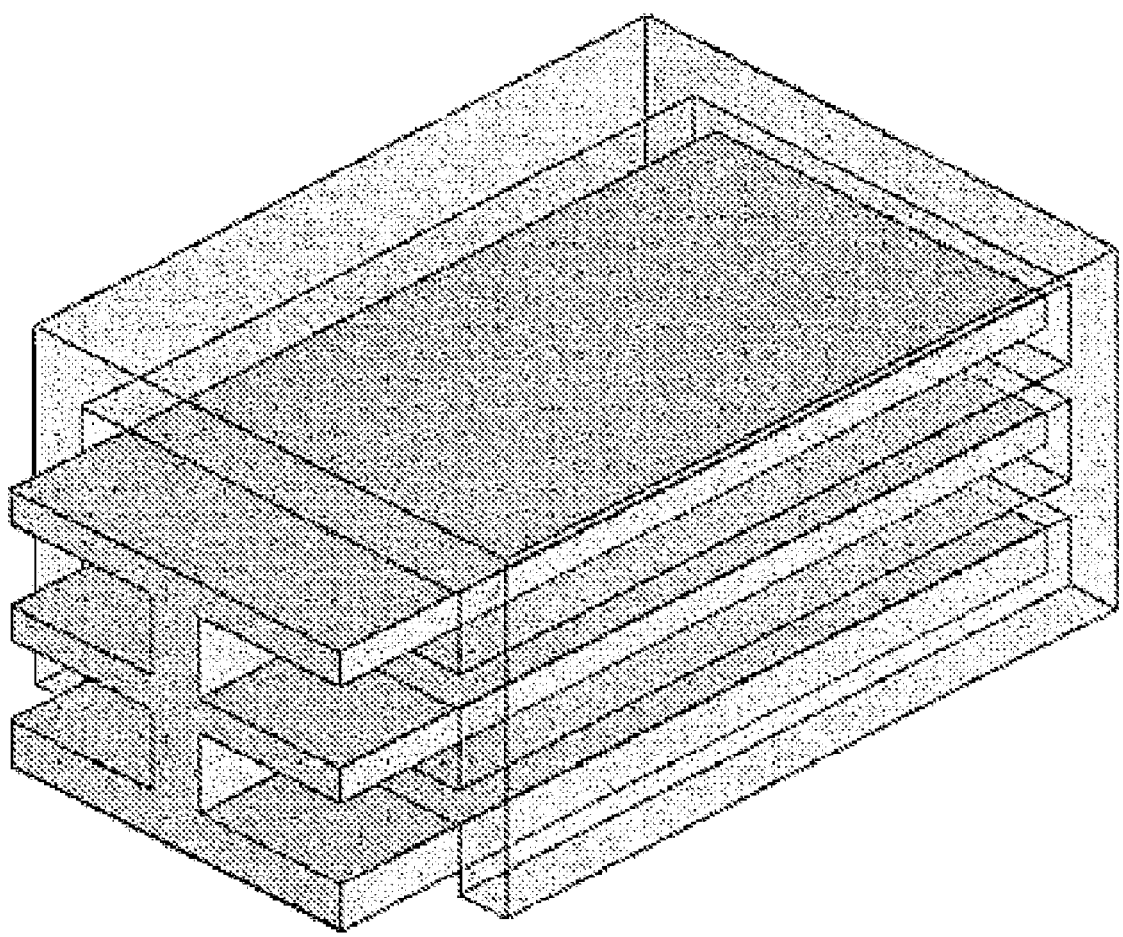
FIG. 19 shows an example of a filter structure formed from stacked planar layers.

While the filter structure of embodiments of the present invention have been described primarily ill terms of having a wafer structure, it will be apparent that suitable filter structures may be made from multiple stacked planar layers, to provide a filter having much longer ion channels than those of a wafer structure. Alternate layers of the stack may be electrically connected in parallel. While a wafer structure is particularly suited to microscale manufacture, a stacked planar arrangement may be achieved using macro scale components, such as metal coated ceramic layers, as well as microscale such as using the EFAB process. Due to the increase in length of ion channels in this embodiment, it is preferable that this embodiment of the invention operates with a combination of gas flow and electric field to drive ions through the channels. A schematic illustration of this filter structure is shown in FIG. 19.

The filter structure of embodiments of the present invention may be driven differentially; that is, the AC component of the transverse field may be applied to opposing sides of the ion channel out of phase.

The ion channel may further comprise inert conductive particles located on the walls thereof; these may be nanoparticles, for example gold nanoparticles. Where the ion channel comprises silicon, over time some oxidation of the surface will occur, altering the electrical properties of the device. The inert particles will not be subject to oxidation, and so will provide a conductive surface for ion contact despite oxidation of the surface of the channel.

A spectrometer made in accordance with the present invention may be coupled to one or more other detection or analysis devices; or the spectrometer may be operated in combination with one or more other analysis techniques. The spectrometer may receive analytes from such a device, or may transfer analytes to said device. Representative additional detection or analysis techniques include mass spectroscopy, gas chromatography, ion mobility spectroscopy, liquid chromatography, capillary electrophoresis, flame ionization detection, thermal conductivity detection, and solid phase microextraction. Any or all of these may be combined with embodiments of the present invention, and exemplary spectrometers of the present invention may also be combined with other spectrometers according to the teachings herein.

Two representative uses of spectrometers made in accordance with the present invention include drug breath analysis, and quality control of wine. For drug breath analysis, the device may be used to detect volatile metabolites originating from the use of a controlled substance in the exhalations of a subject. This would be much quicker and simpler than existing analysis techniques which generally rely on hair, blood, or urine analysis. The metabolites to be detected depend on the substance to be screened for.

Wine is susceptible to taint or corking which impairs the taste and quality of the drink. Corked wine includes a number of contaminants such as tri- and tetra-chloroanisoles, and tri- and tetra-chlorophenols. Spectrometers made in accordance with the present invention may be used to detect these compounds. In some embodiments, a spectrometer may be integrated into a cork-shaped housing intended to sit within the neck of a standard wine bottle, allowing for ready testing of wine samples. A simple red or green light alert may be incorporated into the device to allow rapid reading of results. Alternatively, the device may be incorporated into a wine bottling production line to ensure quality control of the bottling. The device may also be used to sample air drawn over corks before bottling occurs, to check for contaminants in the corks themselves.

Having thus described at least illustrative embodiments of the invention, various modifications and improvements will readily occur to those skilled in the art and are intended to be within the scope of the invention. Accordingly, the foregoing description is by way of example only and is not intended as limiting. The invention is limited only as defined in the following claims and the equivalents thereto.

What is claimed is:

1. A field asymmetric ion mobility spectrometer comprising:
at least one ion channel;
a plurality of electrodes disposed proximate the ion channel; and
electrode control means for controlling the electrodes such that a first drive electric field is generated along the length of the ion channel, and a second transverse electric field is simultaneously generated orthogonal to the first, and wherein each of said plurality of electrodes is involved in simultaneously generating a component of both the drive and transverse electric fields.

2. The spectrometer of claim 1, wherein the drive electric field is a static electric field.

3. The spectrometer of claim 1, wherein the transverse electric field varies over time.

4. The spectrometer of claim 3, wherein the transverse electric field comprises an AC component and a DC component.

5. The spectrometer of claim 1, wherein the electrodes are disposed adjacent the entrance and exit to the ion channel.

6. The spectrometer of claim 1, wherein at least two electrode pairs are provided.

7. The spectrometer of claim 1, further including an ion filter having a plurality of ion channels.

8. The spectrometer of claim 7, wherein the ion channels are defined by a plurality of electrode fingers forming a comb-like arrangement.

9. The spectrometer of claim 7, wherein the filter comprises two or more interdigitated electrode arrays, each array having a plurality of electrode fingers.

10. The spectrometer of claim 7, wherein the filter has a generally wafer-like form.

11. The spectrometer of claim 7, wherein the spectrometer comprises a plurality of functional layers, each layer having a wafer-like form.

12. The spectrometer of claim 1, further comprising one or more of an inlet layer, a dehumidifier layer, and a preconcentrator layer.

13. The spectrometer of claim 1, further comprising a semipermeable membrane.

14. The spectrometer of claim 13 wherein the membrane comprises a heating element.

15. The spectrometer of claim 13 wherein the membrane is in the form of an inlet tube.

16. The spectrometer of claim 1 comprising at least one ion filter.

17. The spectrometer of claim 1 comprising at least one ion detector.

18. The spectrometer of claim 1 further comprising means for generating a gas flow through the spectrometer.

19. The spectrometer of claim 18 wherein the gas flow is a counterflow against the direction of movement of ions.

20. A method for performing ion mobility spectrometry comprising:
passing ions through at least one ion channel having a conductive layer and a plurality of electrodes;
controlling each of the plurality of electrodes such that a first drive electric field is generated along the length of the at least one ion channel, and a second transverse electric field is simultaneously generated orthogonal to the first, and
simultaneously generating a component of both the drive and transverse electric fields involving each of said plurality of electrodes.

* * * * *